United States Patent [19]
Miller

[11] Patent Number: 5,775,826
[45] Date of Patent: Jul. 7, 1998

[54] SAFETY FLUID DISPENSING SYSTEM

[75] Inventor: Frederic Dickson Miller, Rockford, Ill.

[73] Assignee: Siebe North, Inc., Charleston, S.C.

[21] Appl. No.: 655,044

[22] Filed: May 29, 1996

[51] Int. Cl.$^6$ .................... A61M 35/00; A47L 13/34
[52] U.S. Cl. .................. 401/132; 401/133; 604/3
[58] Field of Search ...................... 401/132, 133, 401/134; 604/3

[56] References Cited

U.S. PATENT DOCUMENTS

| | | | |
|---|---|---|---|
| 1,332,985 | 3/1920 | Jarrett | 401/132 |
| 2,371,667 | 3/1945 | Ketner | |
| 3,386,793 | 6/1968 | Stanton | 401/132 |
| 3,403,961 | 10/1968 | Gazzani | 401/202 |
| 3,466,131 | 9/1969 | Arcadi | 401/132 |
| 3,485,562 | 12/1969 | Hidden et al. | 401/134 |
| 3,636,922 | 1/1972 | Ketner | 118/264 |
| 3,768,916 | 10/1973 | Avery | 401/132 |
| 3,998,559 | 12/1976 | Hoyt | 401/132 |
| 4,183,684 | 1/1980 | Avery | 401/133 |
| 4,784,506 | 11/1988 | Koreska et al. | 401/133 X |
| 5,583,353 | 12/1996 | DeHavilland | 401/132 |

*Primary Examiner*—Steven A. Bratlie
*Attorney, Agent, or Firm*—Leydig, Voit & Mayer, Ltd.

[57] ABSTRACT

A fluid dispenser system is disclosed having a suitable spatial separation between a fluid-containing ampule contained therewithin and the user's fingers is provided by a plurality of members extending between the ampule and the user's fingers. The separation prevents shards of glass resulting from breakage of the ampule from cutting the user's fingers. Gripping portions of the dispenser may be profiled or roughened on the surface to provide greater gripping capabilities.

16 Claims, 2 Drawing Sheets

5,775,826

1

SAFETY FLUID DISPENSING SYSTEM

FIELD OF THE INVENTION

This invention relates to disposable applicator packages, such as swabs and the like, for the application of flowable materials to surfaces. Applicators permit fluid materials such as medications and antiseptics to be applied to surfaces such as skin tissue. More particularly, the present invention relates to an applicator package having a combined scrub handle and a porous applicator pad adherent to a peripheral flange of a recessed backing member surrounding a fluid container. The present apparatus has a shape which provides substantial additional protection for users' fingers.

BACKGROUND OF THE INVENTION

U.S. Pat. No. 4,183,684 ('684) to Avery discloses a fluid dispensing unit which can be used for containing and dispensing various fluids and liquids such as medicaments, cleansing agents, cosmetic preparations, polishes, and a generally wide range of liquid materials. The '684 unit includes a body made of a thin flexible material which has a top wall, side walls, and end walls, all forming a recessed housing, and a flange extending around the recess to define an opening at the bottom of the body. The entire body is formed from a thin planar resin-based material. Connected to the flange and in covering position over the recess in body, a porous or spongelike material layer is secured to the body in any of various known manners. Carried within the recess is a frangible ampule containing the fluid to be dispensed throughout the porous body. To release the fluid from the ampule, a bending or squashing force is applied to the thin body side walls so as to fracture the ampule such that the fluid is released thereby into and through the porous member for the intended application. While such a device is satisfactory for its intended purpose, it has a disadvantage in that when the thin side walls are squeezed together to fracture the ampule, and due to the particular configuration, construction, and thinness of the walls, the breaking force applied to break the ampule sometimes causes fractured particles or shards of glass from the broken ampule to become free to penetrate the thin plastic side wall structure, injuring the user's fingers.

The '684 device illustrates a gripping portion that is formed of essentially flat, smooth surface which is separated from the interior ampule solely by the thin planar wall material. That is, only the thin plastic wall material separates the user's fingers from the broken ampule shards.

Dispensing units similar to the general type with which the prior art and the present invention are concerned are known from the '684 patent and certain other U.S. patents.

U.S. Pat. No. 3,403,961 to Gazzani describes a dispensing device which includes a body part which receives and retains a vial containing a liquid to be dispensed. The body further includes a skirted lower portion on which is received a sponge applicator with two body portions having an opening for fluid outflow from the vial. The fluid outflow from the vial is communicated to the sponge. The device is not used with a frangible vial, that is, one that is fractured to release fluid therefrom.

The Staunton U.S. Pat. No. 3,386,793 discloses an applicator for liquids, paste, and like materials which has a flexible compressible housing from which liquid is dispensed through a sponge secured to the bottom of the housing. There is no frangible ampule or vial associated with the device. The fluid containing housing is constructed such that the walls can be squeezed together to a considerable

2 degree so that if it were used with a frangible ampule, there is a strong likelihood that particles of the vial glass could penetrate the wall structure to injure the user.

U.S. Pat. Nos. 2,371,667, 3,636,922 to Ketner, and 3,466,1312 Arcadi disclose various embodiments of fluid applicators in which readily rupturable or frangible fluid-containing unit are housed in association with an absorbent or sponge-like mass. The shapes of devices disclosed are, however, not directed to any strengthening features that would prevent possible penetration by particles of a broken ampule through the side walls.

U.S. Pat. No. 3,768,916 to Avery discloses a scrubbing unit in which a frangible ampule is received in a slot formed in a sponge member and a rigid cap is fitted over the ampule and slot with the sides of the cap being drawn together to compress upper portions of the sponge to facilitate directing outflow of a fluid from the broken ampule and also to limit particles of the broken ampule from passing through the sponge to the user's fingers.

SUMMARY OF THE INVENTION

The present invention is concerned with improvements in a fluid dispensing unit of the type described in the above-mentioned '684 patent. In accordance with the present invention, the dispensing unit which comprises an improved longitudinal housing has top, side, and end walls. The top, side, and end walls define a recess adapted to receive therein at least one fluid containing ampule. The side walls include wall partitions extending between an inner ampule and an outer surface which defines a gripping surface. At the bottom of the recess a flange extends in an encircling course around the bottom opening. It is formed integrally with the side and end walls of the housing. A porous pad member connected to the housing flange covers the recessed opening. The porous pad member can be connected to the underside of the flange in various ways as by a bonded connection wherein the solvent or adhesive or other means can be employed, or the housing and porous pad member can be a heat sealable compatible material and the pad member heat sealed to the flange.

Disposed within the housing are a plurality of transverse sidewall partitions formed in the sidewalls in which both define an interior cradle for receiving an elongated frangible ampule and extend normal to the longitudinal axis to join with a gripping surface. The ampule contains a fluid to be dispensed to and through the porous pad member when the ampule is fractured by a squeezing action applied to the sidewalls of the housing. As provided by the present invention, the structure of the housing is strengthened normal to the longitudinal axis by the transverse wall portions to enhance its rigidity and to provide a space dimension which physically separates the ampule and the gripping surface. This separation includes the region of the housing where manual pressure is applied to break the ampule. Thus, when pressure is applied to fracture the ampule, the user's fingers are and remain separated by the isolation space between the inner and outer portions of the sidewalls created by the transverse wall portions. This isolation space can be provided by alternating convolutions, or indentations, or by wall members extending between ampule and outer gripping surface.

The interstices or crevices between the convolutions and wall members allow the user to have better control over the gripping action by movement of the fingers so that when sufficient pressure has been applied to fracture the ampule, the fingers readily can be withdrawn outwardly to obviate application of such excessive pressure as could result in the sidewalls being pressed into the broken fragments of the glass ampule. Further, even if that should occur, the broken glass fragments would pierce the structure at the inner crevices well away from the user's fingers. In prior art devices the housing structure does not possess such an isolation space as would affirmatively separate the user's fingers from shards of the ampule glass when broken under pressure.

Further, when either the alternating convolutions and/or the transverse wall portions include raised features on the gripping surface, an enhanced gripping surface is provided to insure safe handling of the applicator. Such raised features can be configured to space apart the user's fingers.

In accordance with the invention, the porous pad member can be a sponge layer of a reticulated open cell foam material bonded or laminated to the flange, or a plural ply element including a gauze-like sheet layer with the sheet layer being located immediate or adjacent to the flange. In securing the porous pad member to the underside of the housing flange, it can be bonded in a full, encircling course or it can be heat sealed to the flange.

Further improvements to the present invention are envisioned in variations in the transverse walls. More particularly, some of these transverse walls can be extended inwardly to provide one or more fulcrums for breaking the ampule. One or more of these transverse walls may also be extended outwardly to enhance the users grip, as by forming spaced apart finger indentations.

The foregoing and other objects, features, and advantages of the present invention will be apparent from the following more particular description of the preferred embodiments of the invention, as illustrated in the accompanying drawing figures in which like reference characters refer to the same elements throughout the different views. The drawings are not to scale, emphasis being placed on illustrating the principles of the invention.

BRIEF DESCRIPTION OF THE DRAWING FIGURES

The invention will appear more clearly from a detailed description of the preferred embodiments of the invention to be given in the following description taken together with the accompanying drawings, in which.

Figure 4:
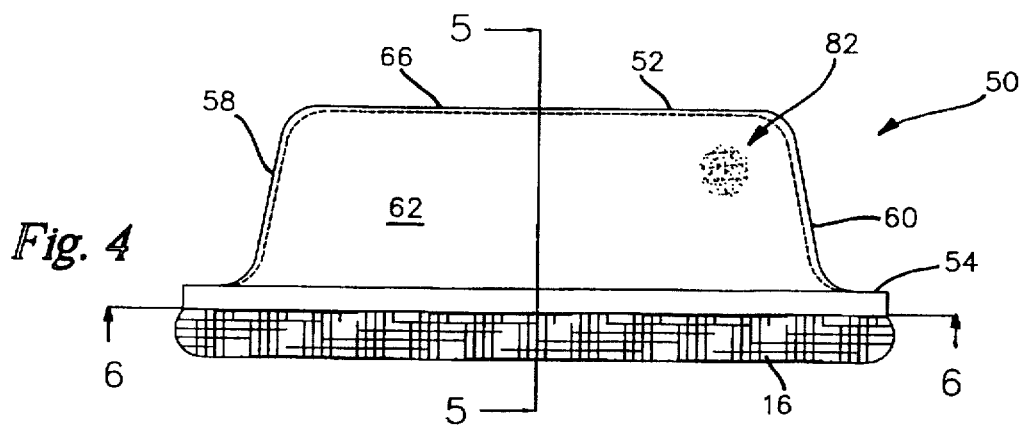
FIG. 4 is a side view of another embodiment of the fluid dispenser of the present invention.
Figure 5:
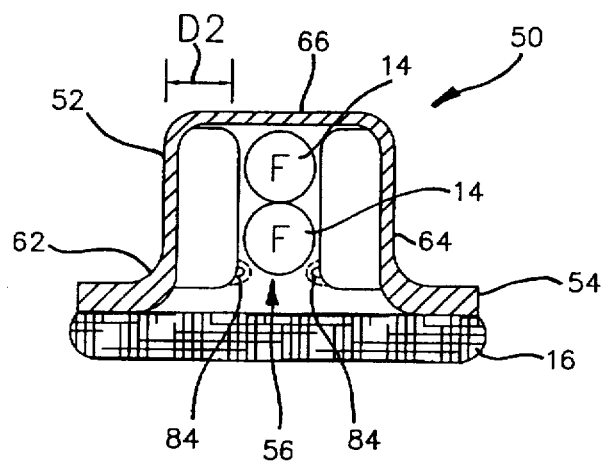
Figure 6:
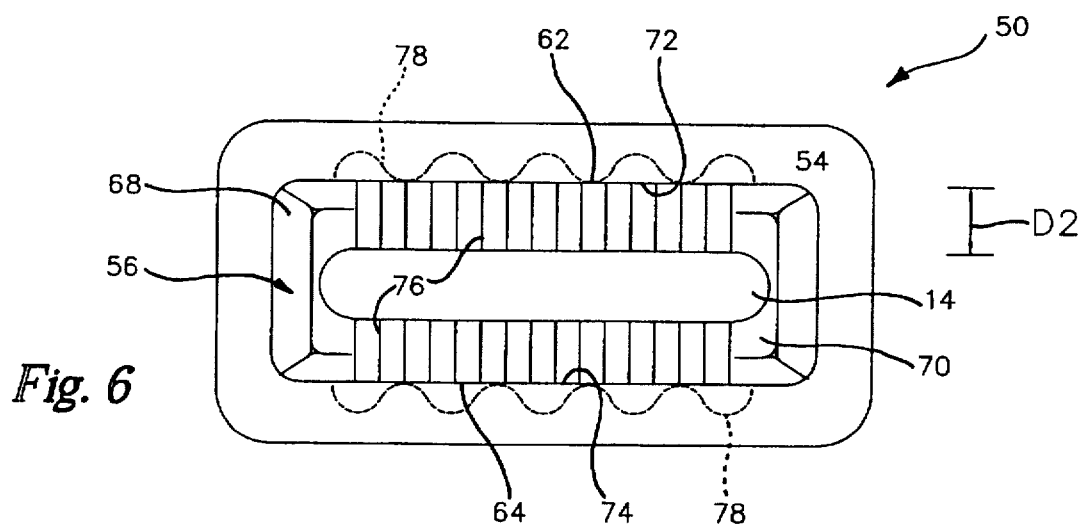

FIG. 5 is a cross section view of the fluid dispenser of FIG. 4 taken along line 5—5 thereof, further including illustration of the disposition of the fluid-containing ampule (s) and illustrating the dimension of the safety spacing; and FIG. 6 is a bottom cross sectional view taken along line 6—6 of FIG. 4 showing the recess of the fluid dispenser illustrating the internal walls that provide safety spacing and the fluid-containing ampule(s).

DETAILED DESCRIPTION OF THE PREFERRED EMBODIMENTS

Figure 1:
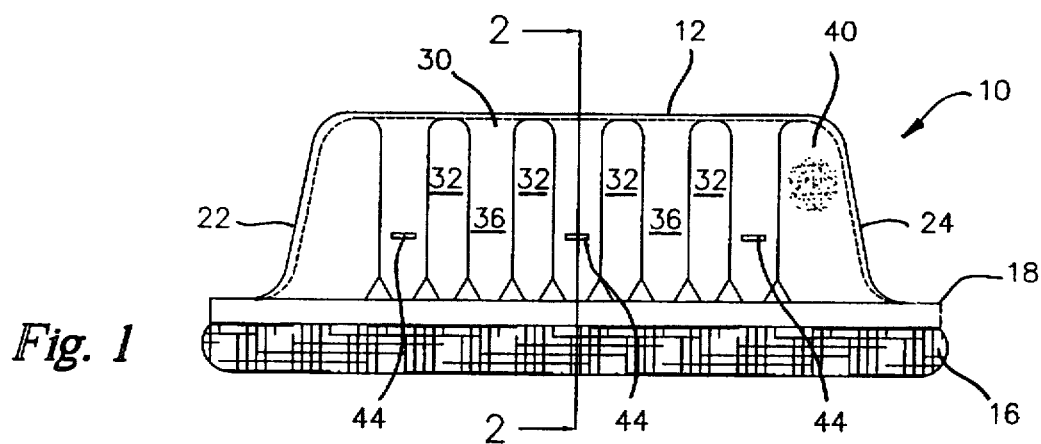
FIG. 1 is a side view of one embodiment of the fluid dispenser of the present invention.
Figure 2:
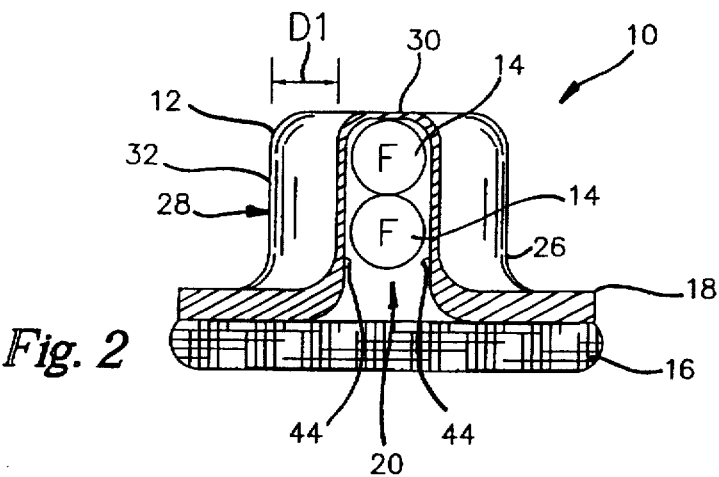
FIG. 2 is a cross section view of the fluid dispenser of FIG. 1, further including illustration of the disposition of the fluid-containing ampule(s) and illustrating the dimension of the safety spacing.
Figure 3:
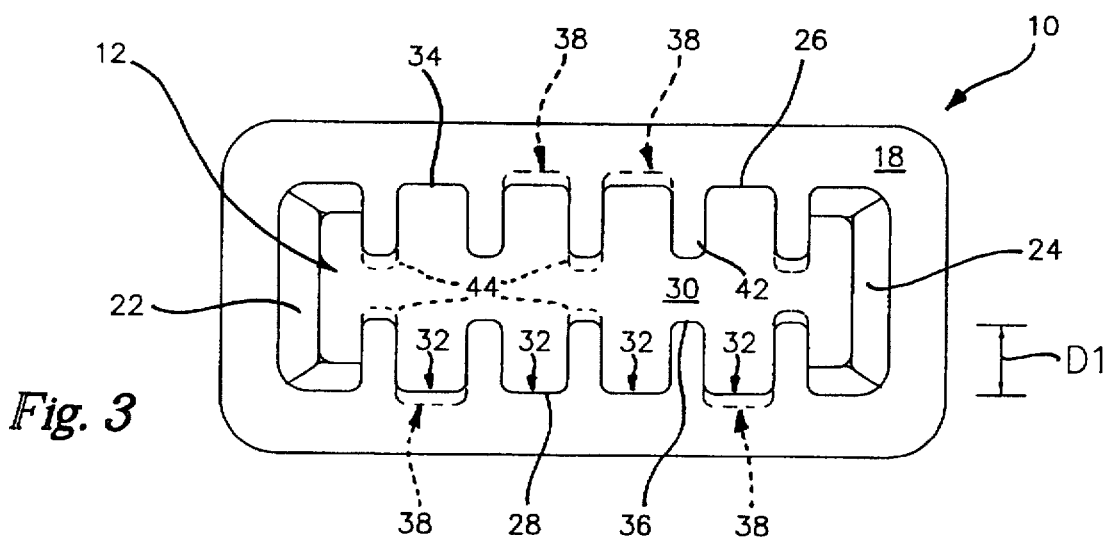
FIG. 3 is a top view of the fluid dispenser of FIG. 1 illustrating the external convolutions providing the safety spacing feature.

Referring now to the drawing figures, wherein the illustrations are for the purposes of showing preferred embodiments of the invention only and not for purposes of limiting the appended claims, there is shown in FIGS. 1–3 an embodiment illustrating the dispenser 10 comprising a housing 12 enclosing one or more ampules 14 containing a fluid F, and a perforate material 16 covering an exposed face of the housing 12.

The housing is elongated along an axis to enclose one or more of the ampules 14. The preferred ampules are sealed tubiform glass containers of antiseptic or other fluid. Housing 12 is recessed from a face lying in a plane defined by a peripheral flange 18 which extends around the recess 20 (FIG. 2). The housing includes first and second end walls 22, 24, longer first and outer second side wall gripping surfaces 26, 28, and a top wall 30. The end walls 22, 24 extend generally normal to the plane of the face 18, but need not extend directly perpendicular therefrom.

Side wall outer gripping surfaces 26, 28 are formed of a plurality of convolutions 32 extending from a plane 34 inwardly to another plane 36. The convolutions 32 are spaced along the length axis on both sides of the housing 12 as is best seen in FIG. 3. The number, width, depth, surface features, and spacing of the convolutions can be varied.

A primary function of the convolutions is to separate the outer gripping surfaces 26, 28 from the glass wall of the ampule(s) 14 by dimension D1. This separation provides a safety space along and within the housing 12 so that when the glass ampule(s) become shattered to release their fluid contents, resulting shards and pieces of the sharp broken glass will not extend to the user's fingers, thus providing a significant measure of protection against laceration of the user's fingers from the glass fragments.

A second function of the outer side wall gripping surfaces is to facilitate gripping by the user's fingers. More specifically, the convolutions forming the gripping surfaces can be configured to enhance the user's grip on the dispenser. This function is achieved in several ways, including by varying the dimension D1 of the convolutions normal to the length axis and their distribution along the length axis to accommodate the user's fingers. For example only, one or more of the convolutions may be extended outward as shown in dotted line form at 38 in FIG. 3. The user's thumb (not shown) can fit between the widely spaced extended convolutions, while the forefinger (not shown) and middle finger (also not shown) are spaced apart by the closely spaced convolutions. Other configurations may be used without departing from the scope of the present invention. Additionally, surface features such as a roughened texture 40 may be added to the gripping surfaces to improve gripping friction.

Not shown in FIGS. 1 and 3, the disposition of the ampule(s) 14 is seen more clearly in FIG. 2. The convolutions 32 extend from the gripping surfaces 26, 28 (and 38, if used) inwardly to the contact surfaces 42 at the ampule(s) 14 by dimension D1. Certain of the inward convolutions extend further to grip the ampule(s) 14 to hold them in place within the housing 12.

A plurality of dimples or indentations 44 are preferably provided to help position the ampule(s) 14 in the recess 20. The extent of the inward projection of the dimples is selected to ensure that the ampule(s) are easily inserted into the recess 20, yet cannot readily fall out if the dispenser 10 housing 12 is inverted. Since it is believed that the outer diameter of the fluid containing ampules 14 may vary somewhat, the extent of the inward projection may require experimental determination, and may vary among different ampule suppliers or over time. The dimples 44 help ensure that the ampule(s) are retained within the recess 20 during the assembly process, and that application of the recess perforate covering material 16 to peripheral flange 18 is unhindered by misplacement of the ampule(s).

The perforate material 16 covering recess 20 is preferably a porous or spongelike material layer. It is secured to the body in any of various known manners, including heat sealing and an adhesive.

There is shown in FIGS. 4–6 another embodiment of the present invention illustrating a dispenser 50 comprising a housing 52 enclosing one or more ampules 14 containing a fluid F, and a perforate material 16 covering an exposed face of the housing 52. A plurality of partial wall portions separate the user's fingers and the ampule. The wall portions can extend inwardly of an exterior gripping surface, or the wall portions can extend outwardly of an interior ampule gripping surface. The former is described in detail hereinafter.

The housing 52 is also elongated along an axis to enclose one or more of ampules 14. Again, the preferred ampules are sealed tubiform glass containers of antiseptic or other fluid F. Housing 52 is recessed from a face lying in a plane defined by a peripheral flange 54 which extends around the recess 56. The housing includes first and second end walls 58, 60, longer first and outer second side wall gripping surfaces 62, 64, and a top wall 66. The end walls 58, 60 extend generally normal to the plane of the face, and need not extend directly perpendicular therefrom. The inner surfaces 68, 70 of end walls 58, 60 are seen in FIG. 6.

Side wall outer gripping surfaces 62, 64 are formed into a comfortable gripping surface, which may be textured or otherwise modified to improve gripping by a user's fingers. In this second embodiment of the present invention, a plurality of partial wall partitions 76 extend inward from the interior surfaces 72, 74 of the side walls 62, 64 (respectively) to the surfaces of the ampule(s) 14. The wall partitions 76 are spaced along the length axis on both sides of the housing 52 interior, as is best seen in FIG. 6, confronting the exterior surfaces of the ampule(s) 14. The number, thickness, inward projection, and spacing of the convolutions can be varied.

A primary function of the wall partitions 76, as with the convolutions 32 of the earlier described embodiment, is to separate the housing inner surfaces 72, 74 from the glass wall of the ampule(s) 14 by dimension D2. This separation provides a safety space along and within the housing 52 so that when the glass ampule(s) become shattered to release their fluid contents, resulting shards and pieces of the sharp broken glass will not extend to the user's fingers, thus providing a significant measure of protection against laceration of the user's fingers from the glass fragments.

The outer side wall gripping surfaces may be adapted to facilitate gripping by the user's fingers. More specifically, the gripping surfaces can be configured to enhance the user's grip on the dispenser. This function is achieved in several ways, such as by varying the cross sectional dimension of the dispenser along its length to accommodate the user's fingers. For example only, the side wall gripping surfaces 62, 64 may be extended outward as shown in dotted line form at 78 in FIG. 6. The user's thumb (not shown) can fit between the spaced bumpouts 78 on one side, while the forefinger (not shown) and middle finger (also not shown) can fit the bumpouts 78 on the other side. Other configurations may be used without departing from the scope of the present invention. Additionally, surface features such as a roughened texture 82 may be added to the gripping surfaces 62, 64 to improve gripping friction.

The disposition of the ampule(s) 14 is seen more clearly in FIG. 5. The partition walls extend from the interior of the gripping surfaces inwardly to the ampule(s) 14 by dimension D2. Certain of the partition walls extend further near the recess 56 face defined by the peripheral edge 54 to grip the ampule(s) 14 and to hold them in place within the housing 52. The extent of the inward projections 84 of these wall portions 76 is selected to ensure that the ampule(s) 14 are easily inserted into the recess 56, yet cannot readily fall out if the dispenser 50 housing 52 is inverted. Since it is believed that the outer diameter of the fluid containing ampules 14 may vary somewhat, the extent of the inward projections 84 may require experimental determination, and may vary among different ampule suppliers or over time. The inward projections 84 help ensure that the ampule(s) 14 are retained within the recess 56 during the assembly process, and that application of the recess perforate covering material 16 to peripheral flange 54 is unhindered by misplacement of the ampule(s).

The perforate material 16 covering the recess 56 is again preferably a porous, spongelike material layer. It is secured to the flange 54 in any of various known manners, including heat sealing and/or with an adhesive.

The method of manufacture of the safety fluid dispensing system is substantially the same for both embodiments disclosed herein. While the description is primarily directed to the first embodiment disclosed, with minor variations discussed below it is equally applicable to the additional embodiment of the invention disclosed herein.

The housings 12 are formed in a conventional mold forming operation from strip material unrolled from a supply material roll; the safety isolation space is formed during the mold forming operation. A plurality CD of housing members 12 can be formed in a single mold forming operation, then advanced to a die and die cut. Alternatively, the housings may also be molded by blow molding, injection molding, or the like, separated if necessary, and readied for transport in bulk to the next step. The housings are then are aligned by loading them into carrier pockets, the ampules are loaded into recesses of the housings, an adhesive is applied to the flanges by an automatic adhesive applicator, and the perforate material is positioned and applied to the housing, covering the respective recesses. The completed fluid dispensers are then extracted from the carrier pockets and subsequently packaged for shipment.

Although certain presently preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

I claim:

1. A safety fluid applicator, comprising a fluid bearing ampule formed of a frangible material; a housing including a generally planar flange portion recessed to a displaced back wall portion joined to the flange portion by an enclosing wall portion to form an inner recess for enclosing the ampule therein; and a perforate material secured to the flange portion so that the fluid flows through the perforate material when the ampule is fractured; wherein the enclosing wall portion includes at least one inner portion defining an ampule receptacle, at least one outer portion defining a gripping surface, and means interconnecting the gripping surface and the ampule receptacle and forming an isolation space for transmitting pressure on the gripping surface to the ampule receptacle to fracture the ampule, the isolation space isolating the gripping surface from the ampule receptacle so that fingers placed on the gripping surface are protected from shards of a fractured ampule.

2. The fluid applicator of claim 1, wherein the interconnecting means comprise a plurality of convolutions extending between the gripping surface and the ampule receptacle to form the isolation space.

3. The fluid applicator of claim 2 having a longitudinal axis, wherein the gripping surface convolutions vary in length normal to the longitudinal axis to form finger recesses distributed along the length of the applicator.

4. The fluid applicator of claim 1, wherein the interconnecting means comprise a plurality of transverse wall partitions extending between the gripping surface and the ampule receptacle to form the isolation space.

5. The fluid applicator of claim 4, wherein at least one of the transverse wall partitions extend to form at least one fulcrum for breaking the ampule.

6. The fluid applicator of claim 1, wherein the gripping surface is a substantially continuous surface and the ampule receptacle is formed by a plurality of inwardly extending wall partitions engaging the ampule.

7. The fluid applicator of claim 1, wherein the gripping surface is substantially planar and the ampule receptacle is formed by a plurality of inner and outer convolutions, wherein the outer convolutions are substantially joined to form the gripping surface and wherein the inner convolutions extend inwardly therefrom to provide gripping contact with the ampule.

8. The fluid applicator of claim 1 having a longitudinal axis, wherein the ampule receptacle is formed by a plurality of inner and outer convolutions, the outer convolutions substantially joined to form the gripping surface, the inner convolutions extending inwardly therefrom to provide gripping contact with the ampule, and the gripping surface varies in distance normal to the longitudinal axis to form finger recesses distributed along the length of the applicator.

9. The fluid applicator of claim 1, wherein the ampule receptacle is a substantially continuous surface in gripping contact with the ampule, and the interconnecting means comprise a plurality of outwardly extending wall partitions to form the gripping surface.

10. The fluid applicator of claim 9 having a longitudinal axis, wherein the outwardly extending wall portions vary in length normal to the longitudinal axis to form finger recesses distributed along the length of the applicator.

11. A safety fluid applicator, comprising a fluid bearing ampule formed of a frangible material; a housing including a generally planar flange portion recessed to a displaced back wall portion joined to the flange portion by an enclosing wall portion to form an inner recess for enclosing the ampule therein; and a perforate material secured to the flange portion so that the fluid flows through the perforate material when the ampule is fractured; wherein the enclosing wall portion includes at least one inner portion defining an ampule receptacle, at least one outer portion defining a gripping surface, and a plurality of convolutions extending between the gripping surface and the ampule receptacle and forming an isolation space for transmitting pressure on the gripping surface to the ampule receptacle to fracture the ampule, the isolation space isolating the gripping surface from the ampule receptacle so that fingers placed on the gripping surface are protected from shards of a fractured ampule.

12. The fluid applicator of claim 11 having a longitudinal axis, wherein the gripping surface convolutions vary in length normal to the longitudinal axis to form finger recesses distributed along the length of the applicator.

13. A safety fluid applicator, comprising a fluid bearing ampule formed of a frangible material; a housing including a generally planar flange portion recessed to a displaced back wall portion joined to the flange portion by an enclosing wall portion to form an inner recess for enclosing the ampule therein; and a perforate material secured to the flange portion so that the fluid flows through the perforate material when the ampule is fractured; wherein the enclosing wall portion includes at least one inner portion defining an ampule receptacle, at least one outer portion defining a gripping surface, and means interconnecting the gripping surface and the ampule receptacle and forming an isolation space for transmitting pressure on the gripping surface to the ampule receptacle to fracture the ampule, the isolation space isolating the gripping surface from the ampule receptacle so that fingers placed on the gripping surface are protected from shards of a fractured ampule, the gripping surface having a substantially continuous surface and the ampule receptacle being formed by a plurality of inwardly extending wall partitions engaging the ampule.

14. A safety fluid applicator, comprising a fluid bearing ampule formed of a frangible material; a housing including a generally planar flange portion recessed to a displaced back wall portion joined to the flange portion by an enclosing wall portion to form an inner recess for enclosing the ampule therein; and a perforate material secured to the flange portion so that the fluid flows through the perforate material when the ampule is fractured; wherein the enclosing wall portion includes at least one inner portion defining an ampule receptacle, at least one outer portion defining a gripping surface, and means interconnecting the gripping surface and the ampule receptacle and forming an isolation space for transmitting pressure on the gripping surface to the ampule receptacle to fracture the ampule, the isolation space isolating the gripping surface from the ampule receptacle so that fingers placed on the gripping surface are protected from shards of a fractured ampule, the gripping surface being substantially planar and the ampule receptacle being formed by a plurality of inner and outer convolutions, the outer convolutions being substantially joined to form the gripping surface, the inner convolutions extending inwardly therefrom to provide gripping contact with the ampule.

15. A safety fluid applicator, comprising a fluid bearing ampule formed of a frangible material; a housing including a generally planar flange portion recessed to a displaced back wall portion joined to the flange portion by an enclosing wall portion to form an inner recess for enclosing the ampule therein; and a perforate material secured to the flange portion so that the fluid flows through the perforate material when the ampule is fractured; wherein the enclosing wall portion includes at least one inner portion defining an ampule receptacle, at least one outer portion defining a gripping surface, and means interconnecting the gripping surface and the ampule receptacle and forming an isolation space for transmitting pressure on the gripping surface to the ampule receptacle to fracture the ampule, the isolation space isolating the gripping surface from the ampule receptacle so that fingers placed on the gripping surface are protected from shards of a fractured ampule, the ampule receptacle having a substantially continuous surface in gripping contact with the ampule, the interconnecting means comprising a plurality of outwardly extending wall partitions to form the gripping surface.

16. The fluid applicator of claim 15 having a longitudinal axis, wherein the outwardly extending wall portions vary in length normal to the longitudinal axis to form finger recesses distributed along the length of the applicator.

* * * * *